United States Patent
Bettenhausen et al.

(10) Patent No.: US 7,341,148 B2
(45) Date of Patent: Mar. 11, 2008

(54) MODULAR CONTAINER FOR THE STORAGE, ORGANIZATION, PROTECTION, STERILIZATION AND DELIVERY OF MEDICAL INSTRUMENTS AND IMPLANTS

(75) Inventors: Todd E. Bettenhausen, Indianapolis, IN (US); Cary A. Bettenhausen, Indianapolis, IN (US)

(73) Assignee: ContainMed, Inc., Speedway, IN (US)

( * ) Notice: Subject to any disclaimer, the term of this patent is extended or adjusted under 35 U.S.C. 154(b) by 205 days.

(21) Appl. No.: 11/135,989

(22) Filed: May 24, 2005

(65) Prior Publication Data

US 2006/0266666 A1    Nov. 30, 2006

(51) Int. Cl.
*B65D 83/10* (2006.01)
*A61B 19/02* (2006.01)
*A61L 2/00* (2006.01)

(52) U.S. Cl. .................. 206/370; 206/439; 422/300

(58) Field of Classification Search ............... 206/370, 206/1.5, 439, 372, 373, 438; 220/324, 326, 220/756, 770, 774; 248/213.2; 422/300
See application file for complete search history.

(56) References Cited

U.S. PATENT DOCUMENTS

| | | | |
|---|---|---|---|
| 4,798,292 A | * | 1/1989 | Hauze ........................ 206/439 |
| 4,915,913 A | * | 4/1990 | Williams et al. ............ 422/119 |
| 5,384,103 A | * | 1/1995 | Miller ........................ 422/310 |
| 5,540,901 A | * | 7/1996 | Riley ........................ 422/300 |
| 5,681,539 A | * | 10/1997 | Riley ........................ 422/300 |
| 5,725,097 A | | 3/1998 | Bettenhausen et al. |
| 5,759,502 A | | 6/1998 | Spencer et al. |
| 5,896,987 A | | 4/1999 | Bettenhausen |
| 6,048,503 A | * | 4/2000 | Riley et al. ................. 422/298 |
| 6,099,812 A | * | 8/2000 | Allen et al. ................. 422/300 |
| 6,116,452 A | * | 9/2000 | Hamel et al. ............... 220/318 |
| 6,164,738 A | | 12/2000 | Dane et al. |
| 6,439,625 B1 | * | 8/2002 | Schainholz et al. ..... 292/307 A |

\* cited by examiner

*Primary Examiner*—J. Gregory Pickett
(74) *Attorney, Agent, or Firm*—Woodard, Emhardt, Moriarty, McNett & Henry LLP

(57) ABSTRACT

A container system for organizing, protecting, sterilizing, storing and delivery of surgical instruments, implants and related devices. An optional cover is removably mounted to a tray and is held thereto by a pair of pivotally mounted handles. Post and button fasteners are removably mounted to the tray and hold rigid and flexible bracketry for securing devices within the assembly.

17 Claims, 17 Drawing Sheets

MODULAR CONTAINER FOR THE STORAGE, ORGANIZATION, PROTECTION, STERILIZATION AND DELIVERY OF MEDICAL INSTRUMENTS AND IMPLANTS

BACKGROUND OF THE INVENTION

The present invention relates generally to the field of containers and cases for holding surgical instruments, implants and devices.

DESCRIPTION OF THE PRIOR ART

Various types of containers and cases have been provided to organize surgical instruments, implants and other medical devices. These items must not only be organized but protected from damage. Likewise, the items must be sterilized, stored and then delivered for ready use. In our U.S. Pat. No. 5,725,097, we have disclosed an instrument cassette and sterile wrap assembly composed of a tray and a lid mounted thereto. In our U.S. Pat. No. 5,759,502 we have disclosed an instrument cassette having a mechanism to prevent lateral movement of the medical instrument when positioned within the cassette. In the U.S. Pat. No. 5,896,987 the tray is provided with downwardly extending feet that are nestable within recesses provided in the tray cover located there beneath. In our U.S. Pat. No. 6,164,738 the storage and sterilization tray assembly is designed to be slidably mounted on a horizontally extending rack.

The sterilization and storage tray assemblies must be modified or tailored to the particular size and configuration of the instruments, implants and devices to be held within the tray. Various types of bracketry and holders are typically mounted within the tray assembly with the configuration of the brackets depending upon the devices to be held within the assembly. In order to utilize the tray assembly in a variety of different applications, it is desirable to provide a tray assembly having internal brackets that may be easily moved or changed depending upon the devices to be held by the brackets. Disclosed herein is such a tray assembly.

SUMMARY OF THE INVENTION

One embodiment of the present invention is a container for use in holding, sterilizing and delivering medical devices and implants comprising a perforated floor having a plurality of floor holes. The floor forms a cavity to receive medical devices and implants. A perforated cover has a plurality of apertures, this cover being removably mounted to the floor. A plurality of mounts with proximal ends are movably mounted to the floor within the cavity at the location of the holes. A plurality of brackets are secured to the mounts to removably hold medical devices and implants within the cavity. A handle assembly is mounted to the floor and has a fixed portion extending over the floor of the cavity and further has a movable portion movable from a first position apart from the fixed portion to a second position beneath and adjacent the fixed portion. The movable portion in the second position is located between the cover and the fixed portion when the cover is mounted to the floor to releasably hold the cover to the floor and transfer lifting force to the floor while isolating and securing the cover.

DESCRIPTION OF THE PREFERRED EMBODIMENT

Figure 1:
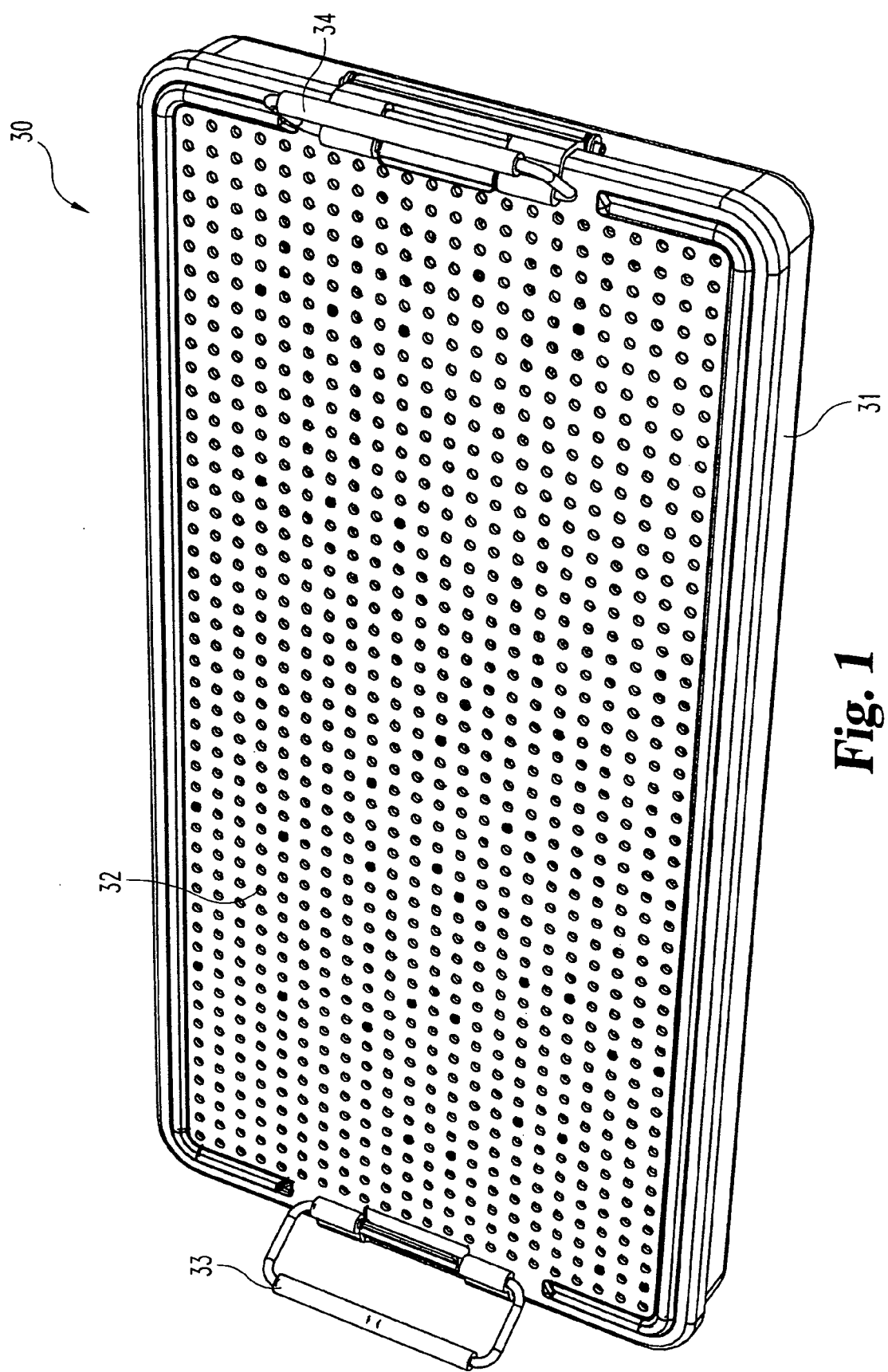
FIG. 1 is a perspective view of a tray assembly incorporating the present invention.
Figure 2:
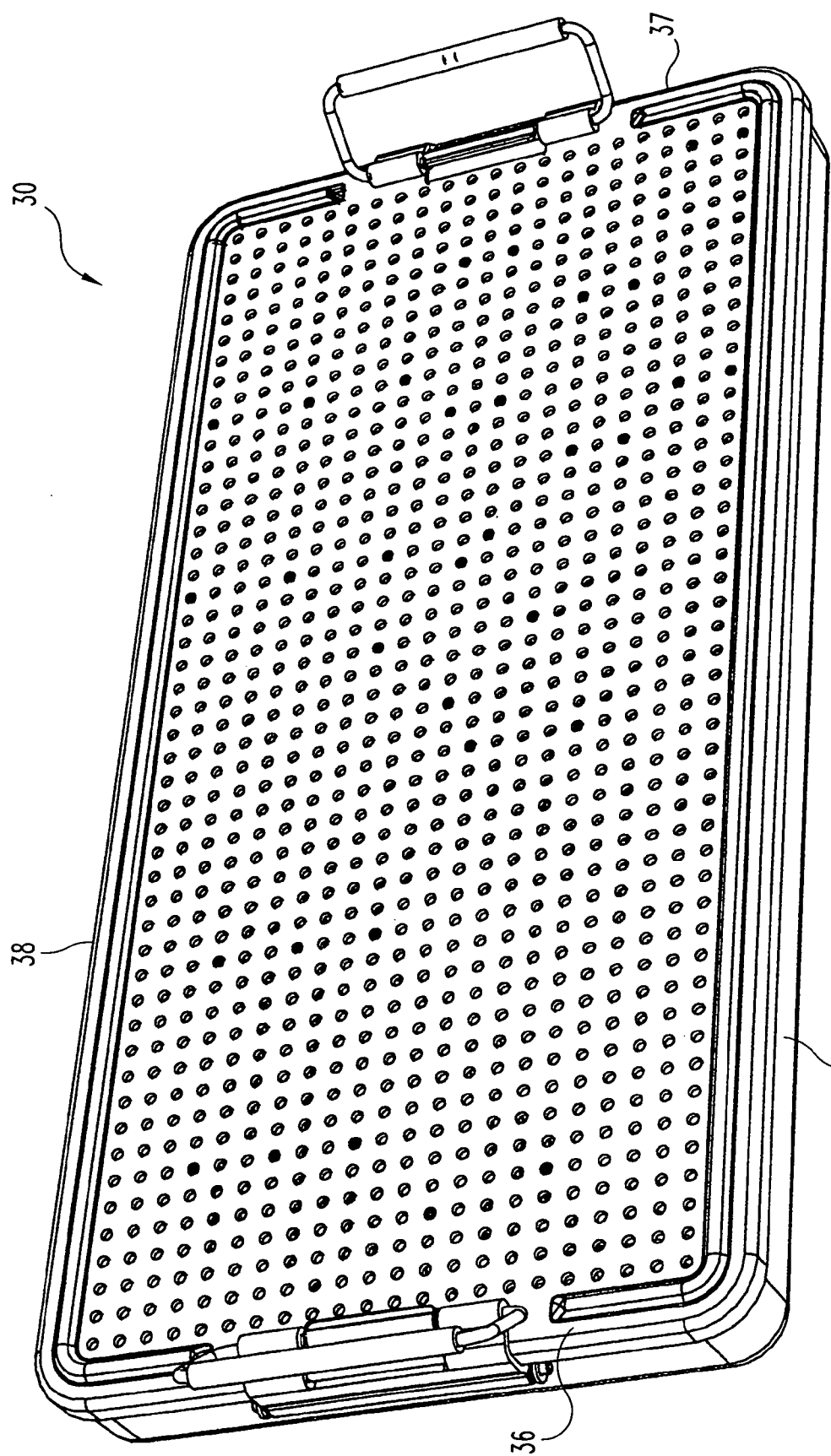
FIG. 2 is the same view as FIG. 1 illustrating the tray assembly from a different perspective.

For the purposes of promoting an understanding of the principles of the invention, reference will now be made to the embodiment illustrated in the drawings and specific language will be used to describe the same. It will nevertheless be understood that no limitation of the scope of the invention is thereby intended; such alterations and further modifications in the illustrated device, and such further applications of the principles of the invention as illustrated therein being contemplated as would normally occur to one skilled in the art to which the invention relates.

Referring to FIG. 1, there is shown a versatile storage and delivery system incorporating the present invention. The system includes a container 30 for the organization, protection, sterilization, storage, and delivery of surgical instruments, implants, and related devices.

Figure 5:
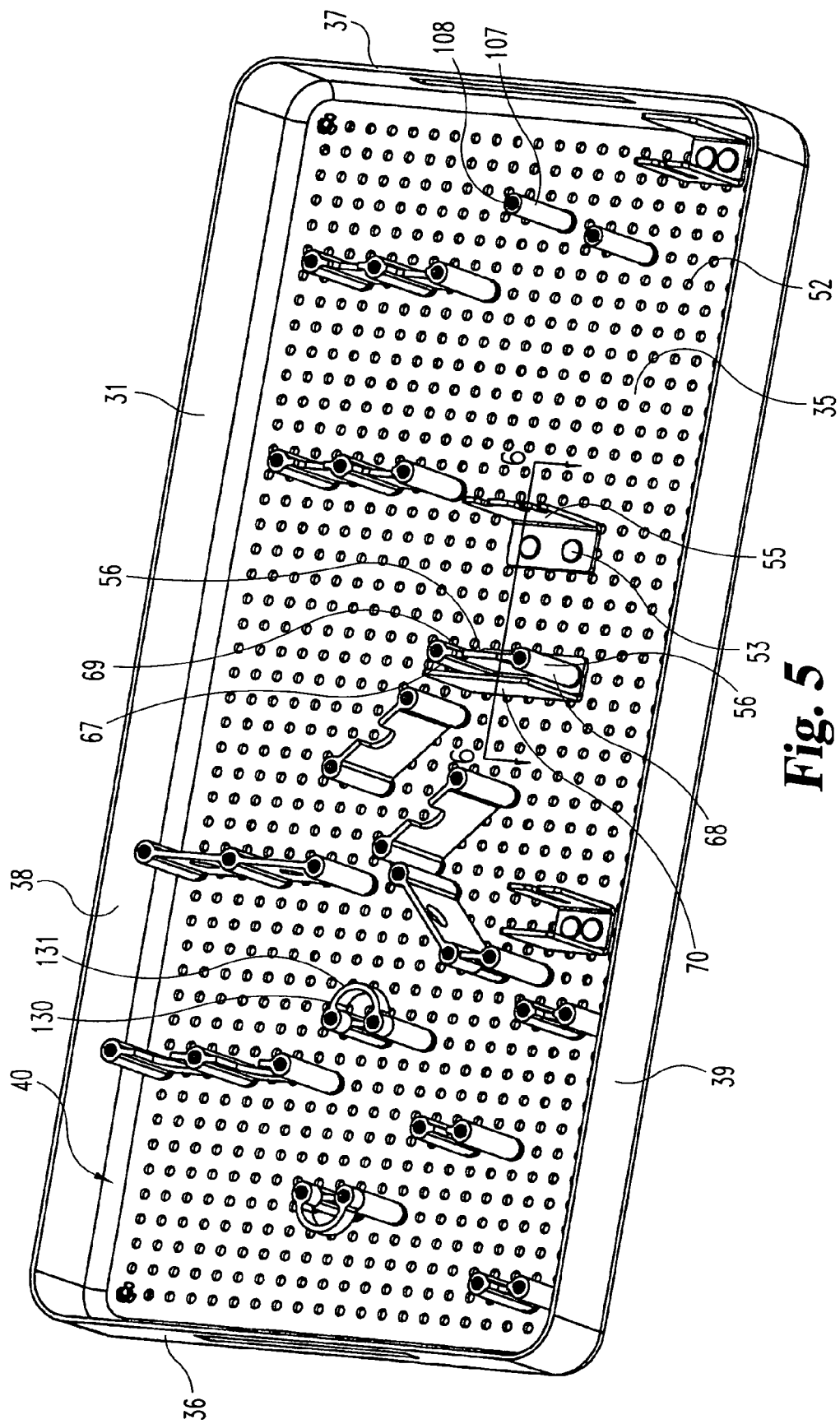
FIG. 5 is a top perspective view of the tray assembly without the cover mounted thereto illustrating examples of internal components located within the tray, as located by the fixture assembly shown in FIG. 4.
Figure 6:
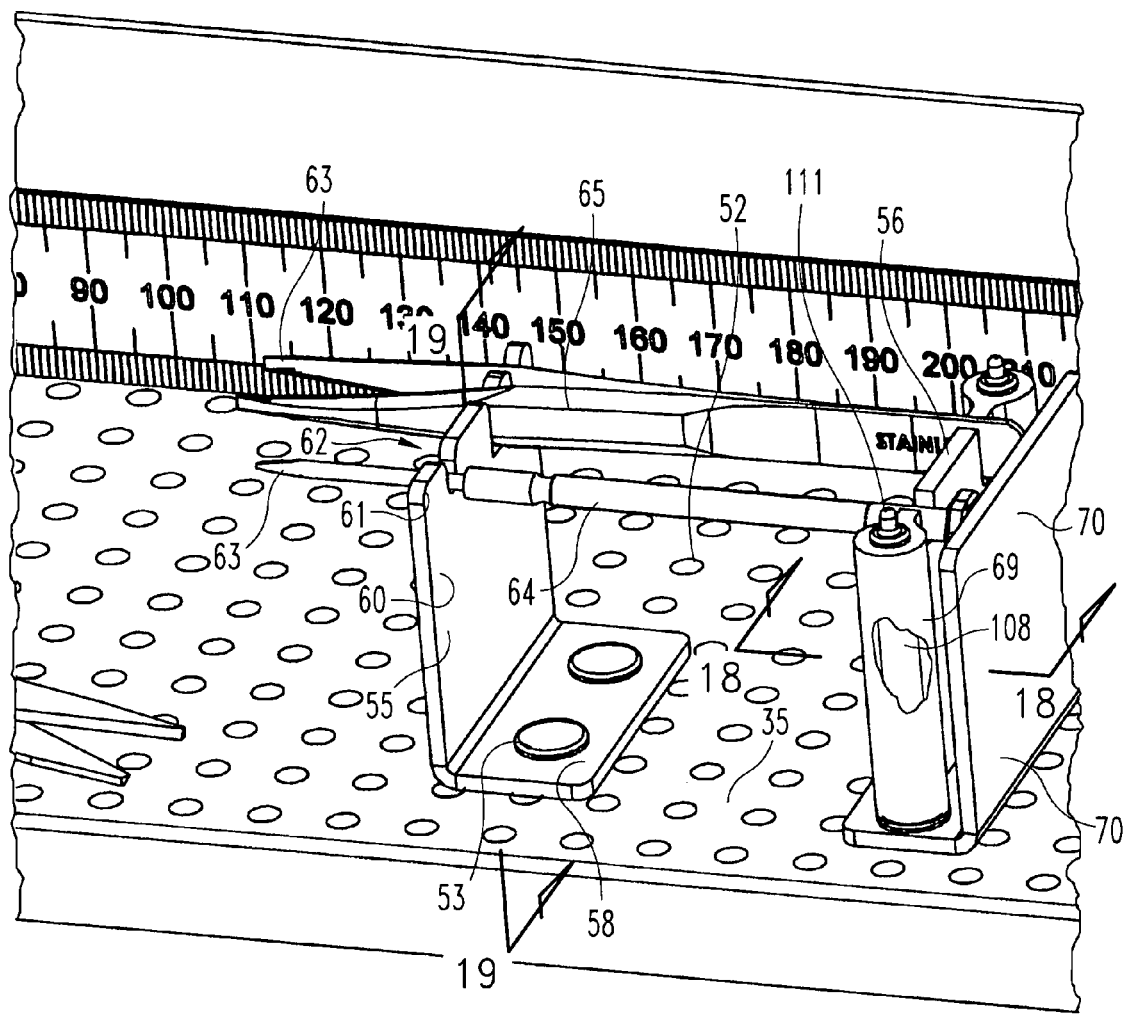
FIG. 6 is an enlarged fragmentary perspective view of two brackets mounted to the tray for holding instruments.

Container 30 includes a perforated tray 31 and an optional, identically perforated cover 32 removably secured thereto by a pair of handle assemblies 33 and 34. The tray 31 (FIG. 5) has a perforated floor 35 joined to a pair of end walls 36 and 37 and a pair of side walls 38 and 39 with the end walls and side walls extending outwardly from the floor forming a cavity 40 into which may be located surgical instruments, implants and related devices.

Movable internal posts and buttons are located within the tray and retain rigid and flexible brackets and supports for holding the surgical instruments, implants and related devices within the tray. A fixture is first used to hold the posts in position for subsequent installation within the tray.

Figure 3:
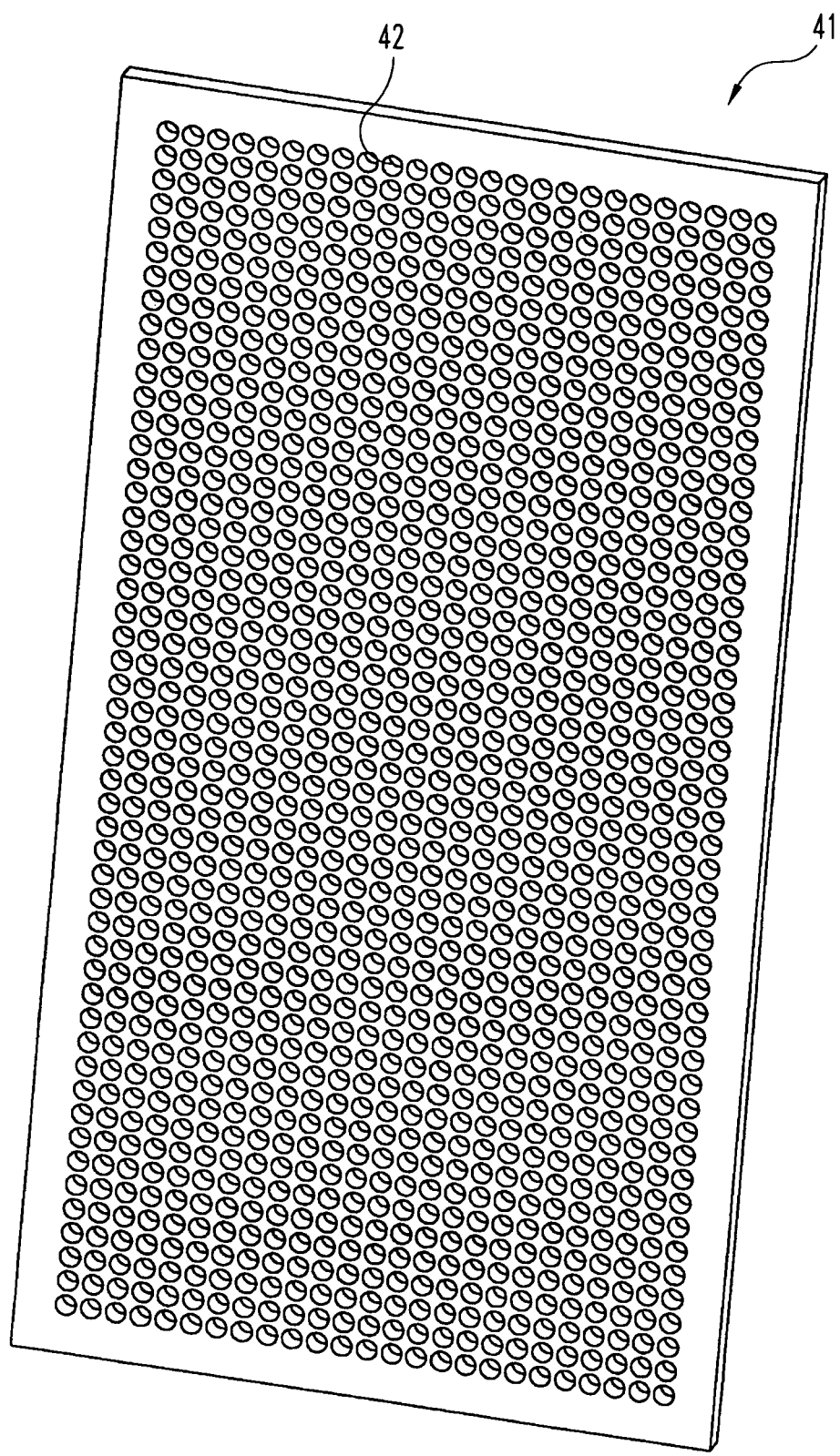
FIG. 3 is a front perspective view of a fixture utilized in installing internal components within the assembly of FIG. 1.

Fixture 41 (FIG. 3) is a flat plate having a plurality of holes 42 matching and alignable with the plurality of holes 52 provided in floor 35 (FIG. 5) of the tray. The tray and components may be assembled prior to shipment and use. Fixture 41 is utilized to configure or reconfigure the tray to the particular use.

Figure 8:
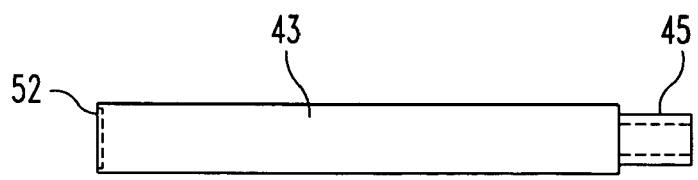
FIG. 8 is an enlarged view of one embodiment of a fixture post.
Figure 15:
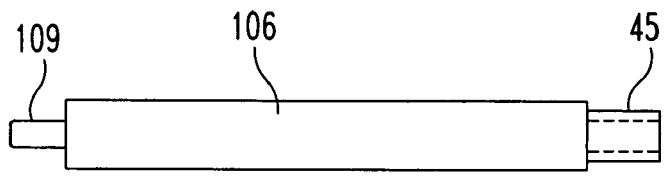
FIG. 15 is an enlarged view of another embodiment of a fixture post.
Figure 16:
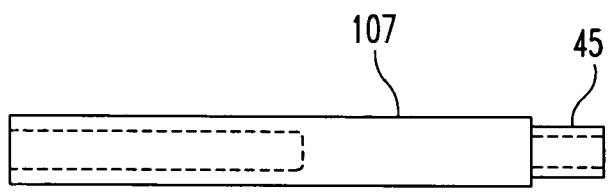
FIG. 16 is an enlarged view of yet another embodiment of a fixture post.

A plurality of cylindrical fixture posts 43, 106 & 107 (FIGS. 8, 15 & 16) are mounted to fixture 41. Each post 43, 106 & 107 includes a reduced diametered first end 45 sized to closely fit through holes 42 of fixture 41. Ends 45 are removably mounted to fixture 41 by conventional means. For example, each end 45 may have an internally threaded hole to receive a threaded bolt, the head of the bolt preventing disengagement of the post from the fixture. Likewise, a variety of snap rings and other devices may be used. As an alternative, external threads may be provided on ends 45 that extend through the fixture being threadedly received by internally threaded nuts provided on the opposite side of the fixture.

Figure 4:
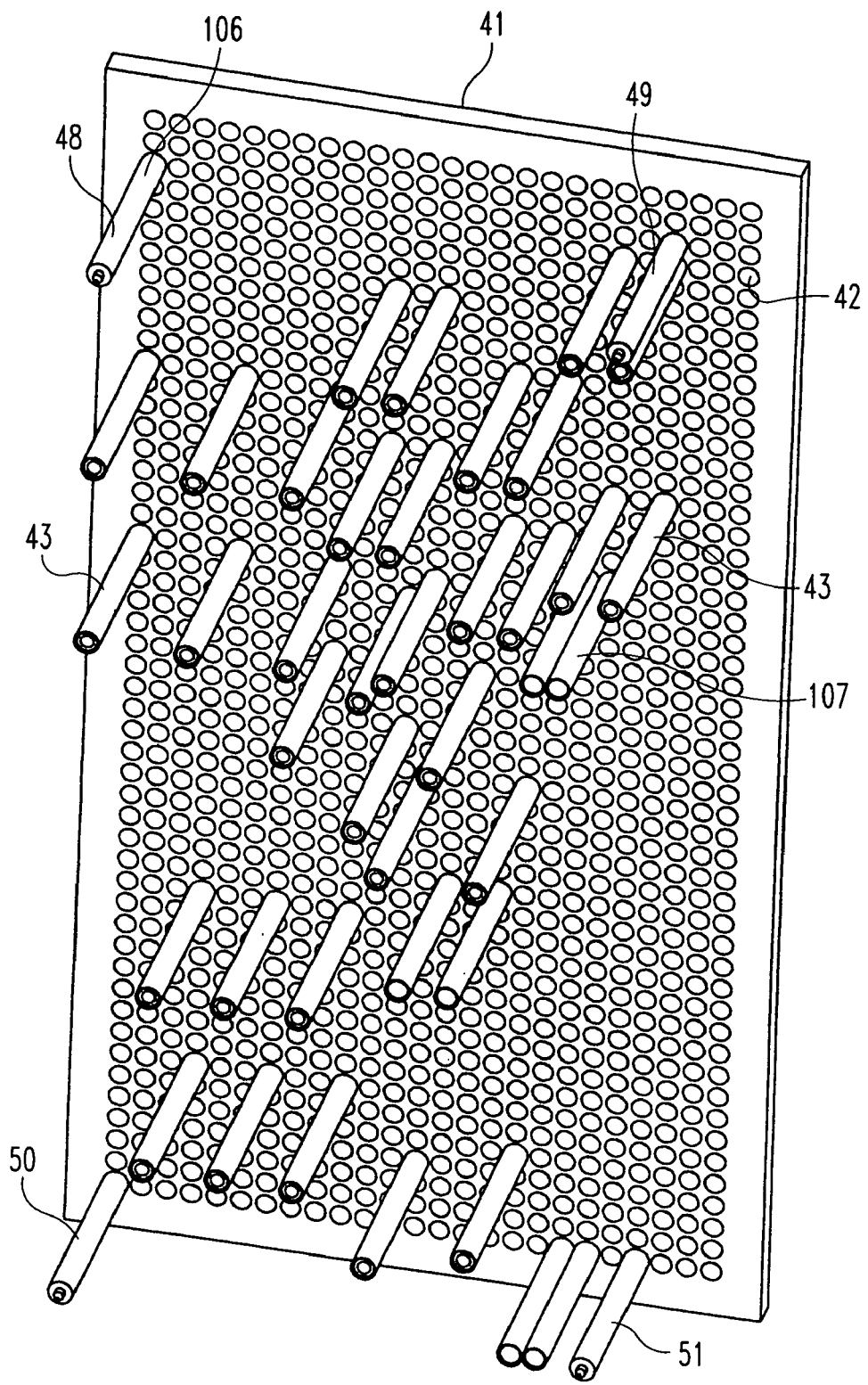
FIG. 4 is the same view as FIG. 3 only showing vertical posts mounted to the fixture and used to locate and assemble internal components within the tray assembly.

Fixture 41 is placed on a supporting work surface, such as a bench, etc., with the posts 43, 106 & 107 facing outward in the same direction as depicted in FIG. 4. Posts 106 serve as alignment posts with respect to the fixture and tray 31. In the embodiment depicted in FIG. 4, four such posts 106 are utilized and are shown as posts 48, 49, 50 and 51. These four posts are spaced apart to be positioned in the four corners of tray 31. The outer distal end 109 (FIG. 15) of each post 106 has a reduced diameter to extend through the holes 52 of the tray floor 35 once the tray is inverted and temporarily mounted to the outwardly extending posts of fixture 41.

Figure 9:
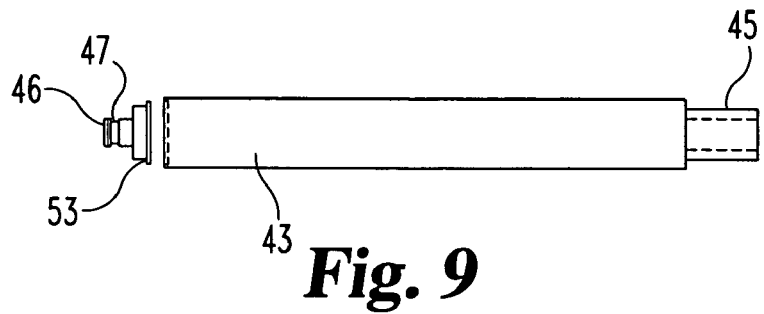
FIG. 9 is the same view as FIG. 8 only with a fastening button shown positioned to be inserted on the post for installation on the tray.

Fixture posts 43 have ends 52 that are counter bored to receive the heads of button fasteners 53 (FIG. 9) with the shanks 46 extendable through the tray floor 35. Shanks 46 have grooves 47 to receive snap rings or may be externally threaded to receive an internally threaded fastener. Fixture posts 43 are used to install the button fasteners 53 on the tray as will be described latter in this specification.

Fixture posts 107 (FIG. 16) are hollow and internally sized to slidably receive bracket mounting posts 108 (FIG. 17) Once posts 43, 106 and 107 are mounted to the fixture, the bracket mounting posts 108 are positioned in the hollow fixture posts 107 and button fasteners 53 are positioned in the ends 52 of fixture posts 43.

Bracket mounting posts 108 are solid and include a cylindrical body with opposite ends 111 and 112. End 111 has a reduced diameter and is sized to fit through the optional cover 32 when mounted to tray 31. Post 108 has enlarged portions 113 and 114, that are ring-shaped in the preferred embodiment, adjacent ends 111 and 112 that act to restrain a flexible bracket mounted thereon and to be described later in this specification. End 112 has a reduced diameter portion 118 extendable through the floor of the tray with a groove 115 provided thereon to receive a retaining ring mounting the post to the tray floor. Other techniques may be utilized to secure post 108 to the tray floor. A variety of retaining rings are available. For example, one such ring is available from Truarc Company, LLC, 70 East Willow Street, Millburn, N.J., under Truarc Part No. 5304-15. Other means may be utilized to secure ends 112 and 46 to floor 35, such as described for the attachment of end 45 to fixture 41.

Post portion 116 (FIGS. 17 and 18) has a diameter greater than end 112 forming shoulder 110 but less than the main body of the post forming shoulder 117. Shoulder 117 abuts against the upwardly facing surface of wall 120 of bracket 70 whereas shoulder 110 abuts against the upwardly facing surface of floor 35 thereby cooperatively with the retaining ring on the opposite side of the tray floor holding the post in an upright and fixed position.

Posts 108 and button fasteners 53 (FIG. 5) are used to removably mount a plurality of flexible brackets 56 and rigid brackets 55 and 70 to the floor 35 of the tray. Button fastener 53 is designed to hold planer surfaces in mated contact including but not limited to rigid brackets and overlapping joints, such as those present at the corners of enclosures fabricated from folded sheet. Post 108 provides a cylindrical projection that occupies most of the vertical distance between floor 35 and the optional cover and locates the flexible brackets using the passages present at the ends of the brackets. Alternatively, posts 108 extend through the mid or other points of the brackets. The flexible and rigid brackets removably hold the various surgical instruments, implants and other devices in the tray.

Figure 19:
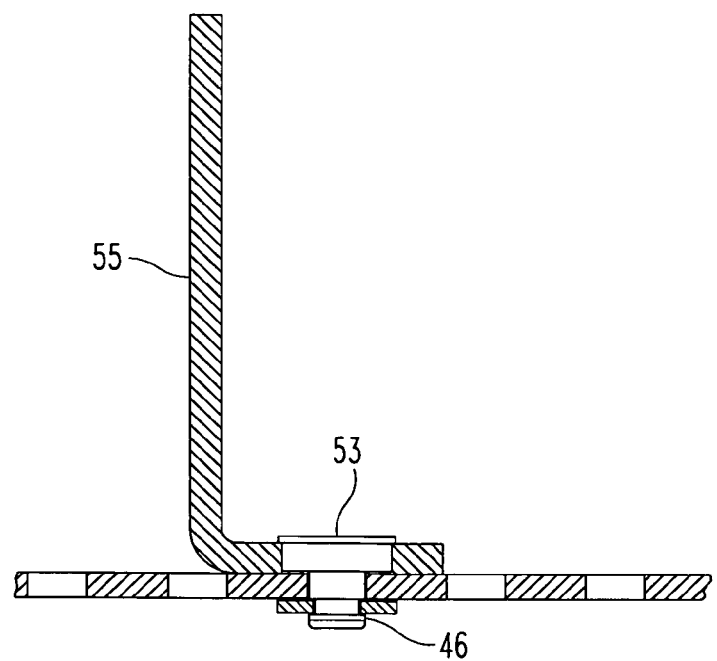
FIG. 19 is a cross sectional view taken along the line 19-19 of FIG. 6 and viewed in the direction of the arrows.

As an example, right angle rigid bracket 55 (FIG. 5) has a first wall 58 parallel to and removably mounted atop floor 35 by a pair of button fasteners 53 having an enlarged head positioned adjacent wall 58 with the end 46 (FIG. 19) of each button fastener extending through wall 58 and holes 52 of floor 35. A variety of techniques may be used to removably secure the shank of the button fastener to floor 35. For example, the shanks may be externally threaded and receive internally threaded nuts positioned on the opposite side of floor 35. The vertically extending bracket wall 60 includes a top end 61 with openings 62 formed therein to releasably receive and hold the ends 63 of items 64 and 65. The shape and configuration of openings 62 may be varied depending upon the size and configuration of the instrument, implant or other device to be held by the bracket.

Figure 17:
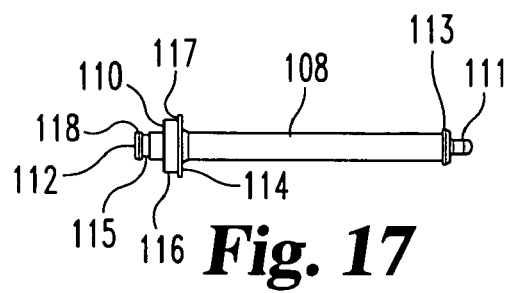
FIG. 17 is an enlarged view of a bracket mounting post.
Figure 18:
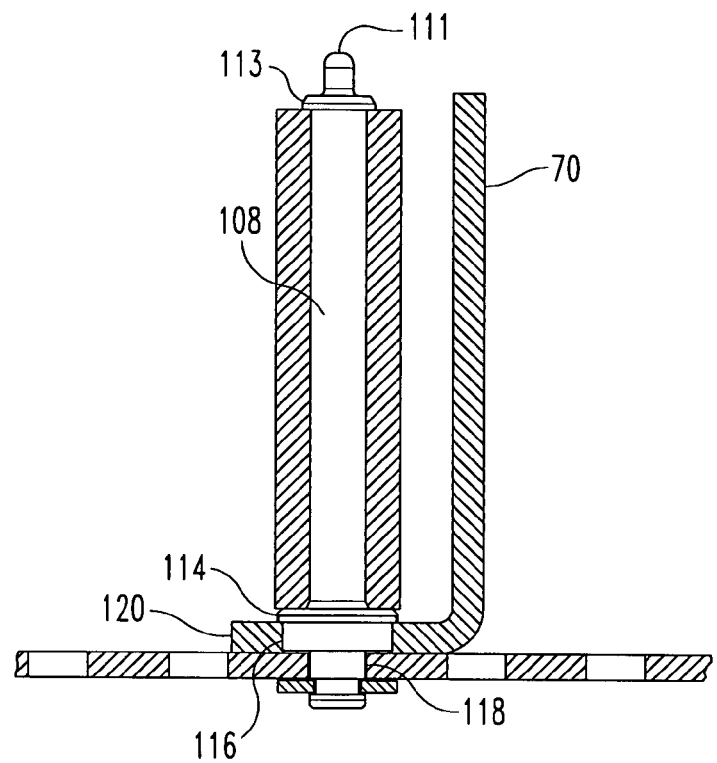
FIG. 18 is a cross sectional view taken along the line 18-18 of FIG. 6 and viewed in the direction of the arrows.

The flexible brackets are configured to removably receive and hold the variety of instruments and devices positioned within the tray. For example, flexible bracket 56 (FIG. 5) includes a flexible web 69 integrally joined to a pair of cylindrical ends 67 and 68 each having a passage extending therethrough to removably receive a post 108. The top end of web 69 is provided with a recess or hole to removably receive and hold the particular instrument or device within the tray. The flexible casing forming ends 67 and 68 are slipped over and around post 108 so that the top and bottom of ends 67 and 68 (FIG. 5) rest adjacent enlarged portions 113 and 114 (FIG. 17). The bottom end of post 108 extends through the floor 35 and may be secured thereto by an external retaining clip. The top end of post 108 has a reduced diameter top end to fit into the holes of any cover or tray stacked atop the post. Bracket 70 has an upstanding wall having a solid surface against which the ends of tools 64 and 65 may abut.

Fixture posts 43, 106 & 107 are mounted to fixture 41 and bracket mounting posts 108 are positioned within fixture posts 107, button fasteners 53 are positioned in ends 52 of posts 43 and rigid brackets 55 and 70 are mounted to posts 43 so ends 46 of button fasteners 53 extend through the brackets. Tray 31 is then positioned atop the posts so ends 46, 109, and 112 of the posts and button fasteners extend through the floor of the inverted tray with the ends 46 and 112 then being secured to the floor by the fastening means previously described. Tray 31 is then removed from fixture 41 along with its posts 43, 106 and 107 and the flexible brackets are slipped onto posts 108.

Figure 7:
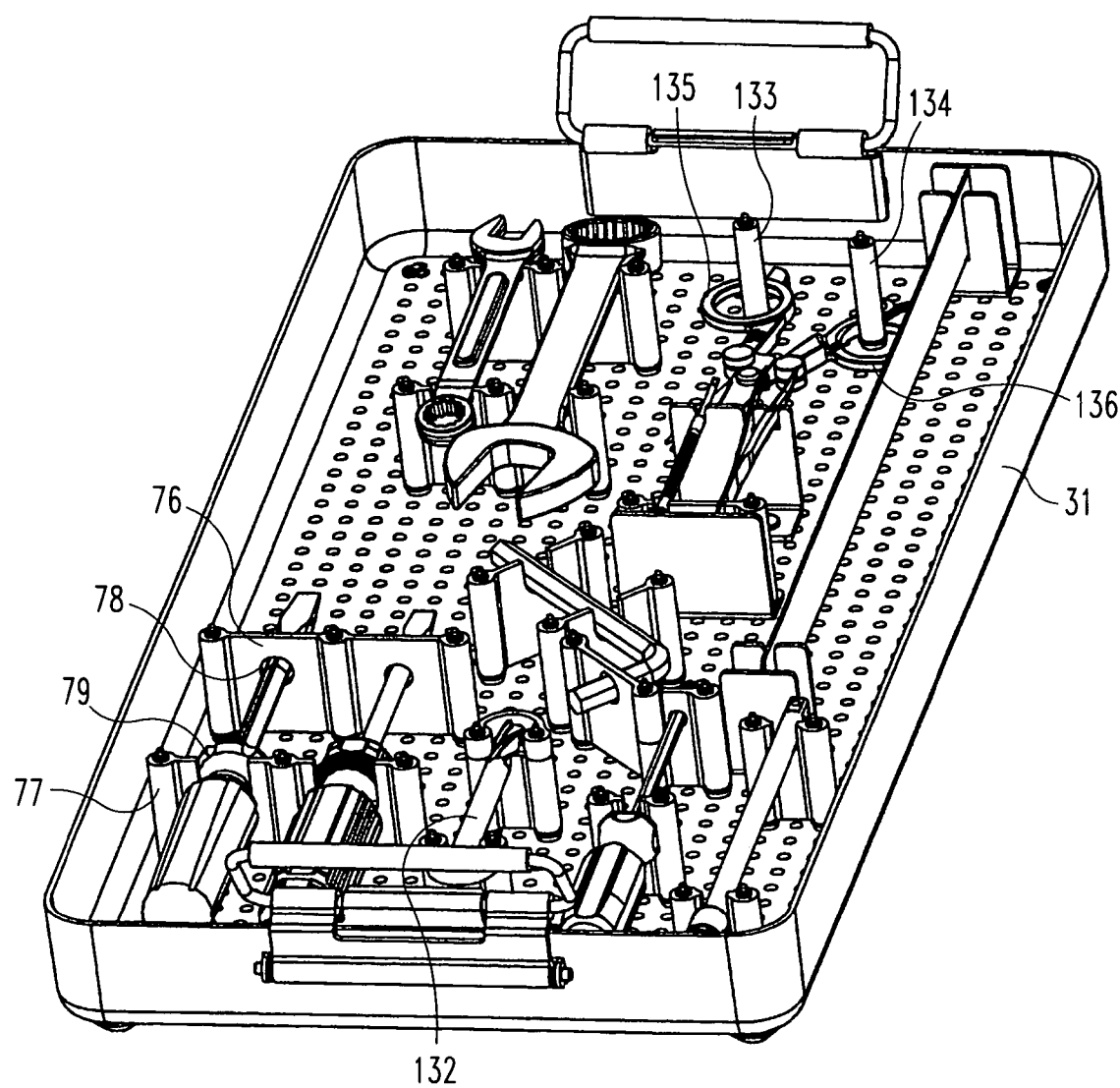
FIG. 7 is a top perspective view of an assembled tray having a variety of tools retained within with the tools shown being non-medical tools simply for illustration purposes only.

The flexible and rigid brackets are configured depending upon the instrument or device to be held within the tray. For example, flexible brackets 76 and 77 (FIG. 7) are mounted by vertical posts 108. Bracket 76 includes a hole 78 through which the shank of a screw driver extends whereas bracket 77 includes an upwardly opening recess to receive the handle 79 of the screw driver. Brackets 76 and 77 are designed to each receive three vertical posts thereby allowing for the mounting of a pair of screw drivers. The tools shown in FIG. 7 are for illustration purposes only.

The top end 111 of post 108 is extendable through the optional cover 32 (FIG. 1) or optional insert tray identical to and positioned above tray 31 thereby reinforcing the post and the surrounding floor and preventing any deformation by inertial forces generated by movement of the instruments and devices held within the tray.

Posts 108 extend from the floor 35 of tray 31 to cover 32 thereby allowing the ends 67 and 68 (FIG. 5) of the flexible brackets to extend with integral flexible web 69 from floor 35 to cover 32. Prior flexible brackets typically hold the various surgical instruments, implants and related devices in a press fit relationship since the brackets did not extend to the underside of the cover, preventing utilization of the cover for vertical retention. Concerns therefore exist relative to cleaning and sterilization issues existing between a tight fitting bracket relative to the device held by the bracket. The flexible brackets disclosed herein are produced from silicone and are supported along their entire height from floor to cover allowing the openings in the integral web 69 to loosely receive and hold the surgical instruments, implants and related devices providing for superior sterilization results. Further, the silicone brackets completely encase posts 108 preventing damage to the devices held by the brackets by preventing the devices from contacting the posts as compared to conventional brackets and metal posts not encased in silicone or other protective coatings.

Figure 10:
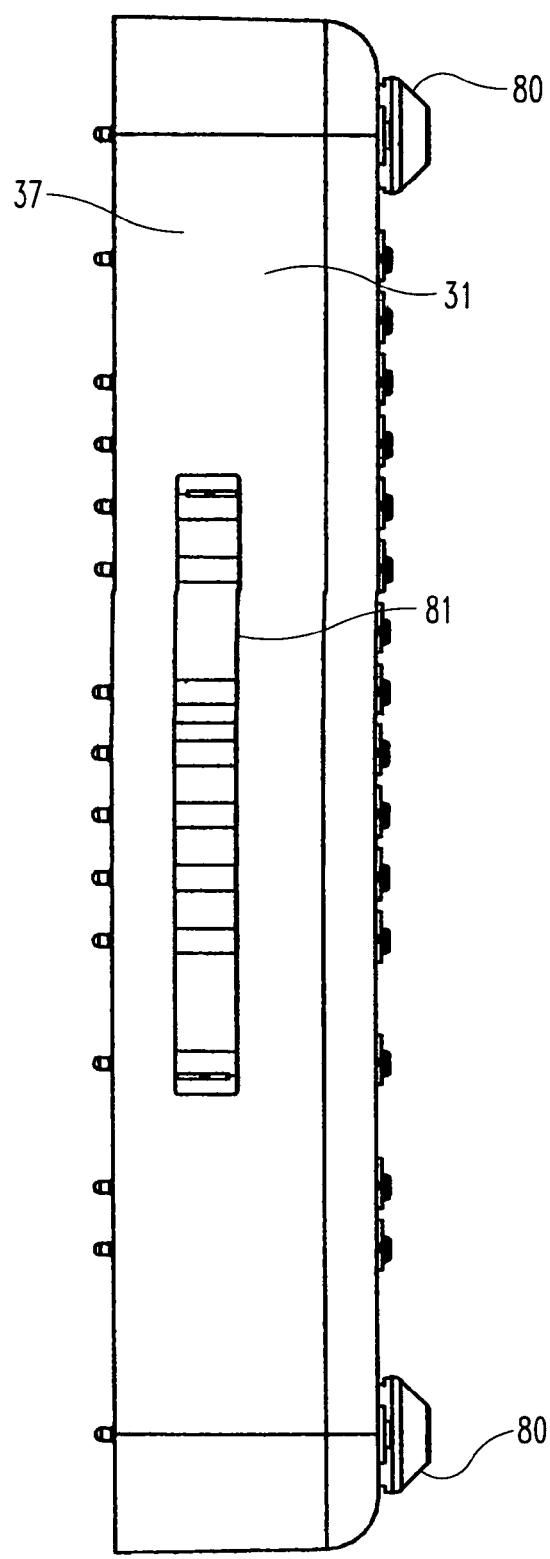
FIG. 10 is an enlarged end view of the tray of FIG. 5.

A plurality of external stacking feet 80 (FIG. 10) are provided on the under surface of tray 31. The stacking feet may be cast, machined or molded from any suitable material and serve to elevate the system when placed upon sterile drape used to cover work surfaces at the point of use. The feet 80 also serve to locate stacked systems atop one another by nesting within features present on the system cover 32. The general shape of each foot allows the system to be placed upon or removed from wire racks without snagging and presents soft contours minimizing the possibility of puncturing sterile wrap. The foot 80 is ideally fastened to the floor 35 of the container using the same retaining clip found elsewhere in the system, and may or may not contain features to allow placement of internal components in perforations adjacent to that in which the foot is affixed. The feet may be placed in any unoccupied perforation. At minimum, diagonally opposed feet are required for proper stacking. In the embodiment shown in FIG. 10, each foot 80 has a truncated conical shape with an upper pin (not shown) extending upwardly through the holes 52 of the bottom floor 35 of tray 31. The pins of the feet may then be secured to floor 35 by any suitable means, such as the retaining clips, threaded bolts or internally threaded nuts.

Handle assemblies 33 and 34 (FIG. 1) are attached to the opposite end walls of tray 31. End walls 36 and 37 have rectangular openings to facilitate the mounting of the assemblies.

Figure 11:
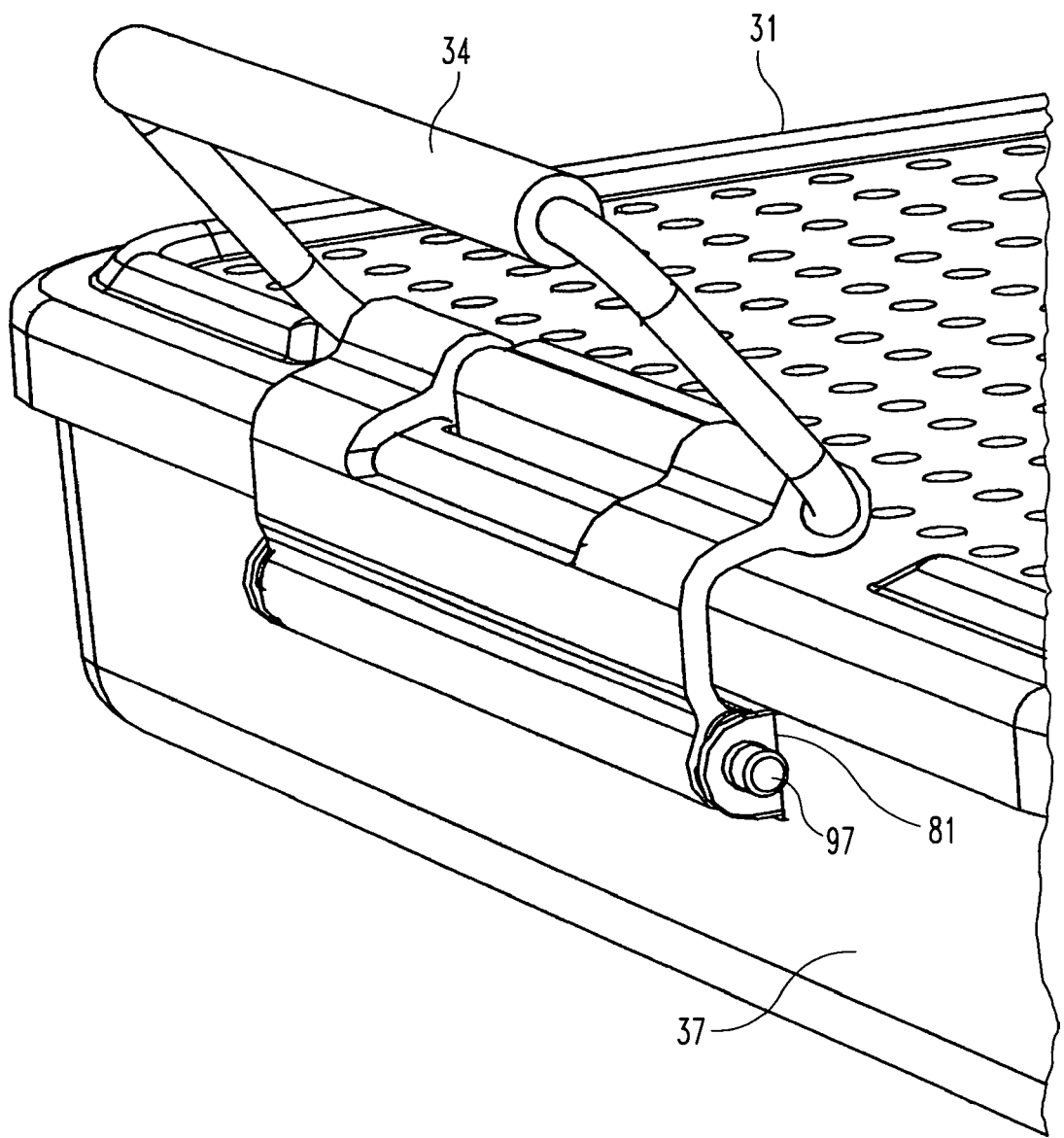
FIG. 11 is an enlarged fragmentary perspective view of one end of the tray including the cover and showing a handle mounted to the tray.
Figure 12:
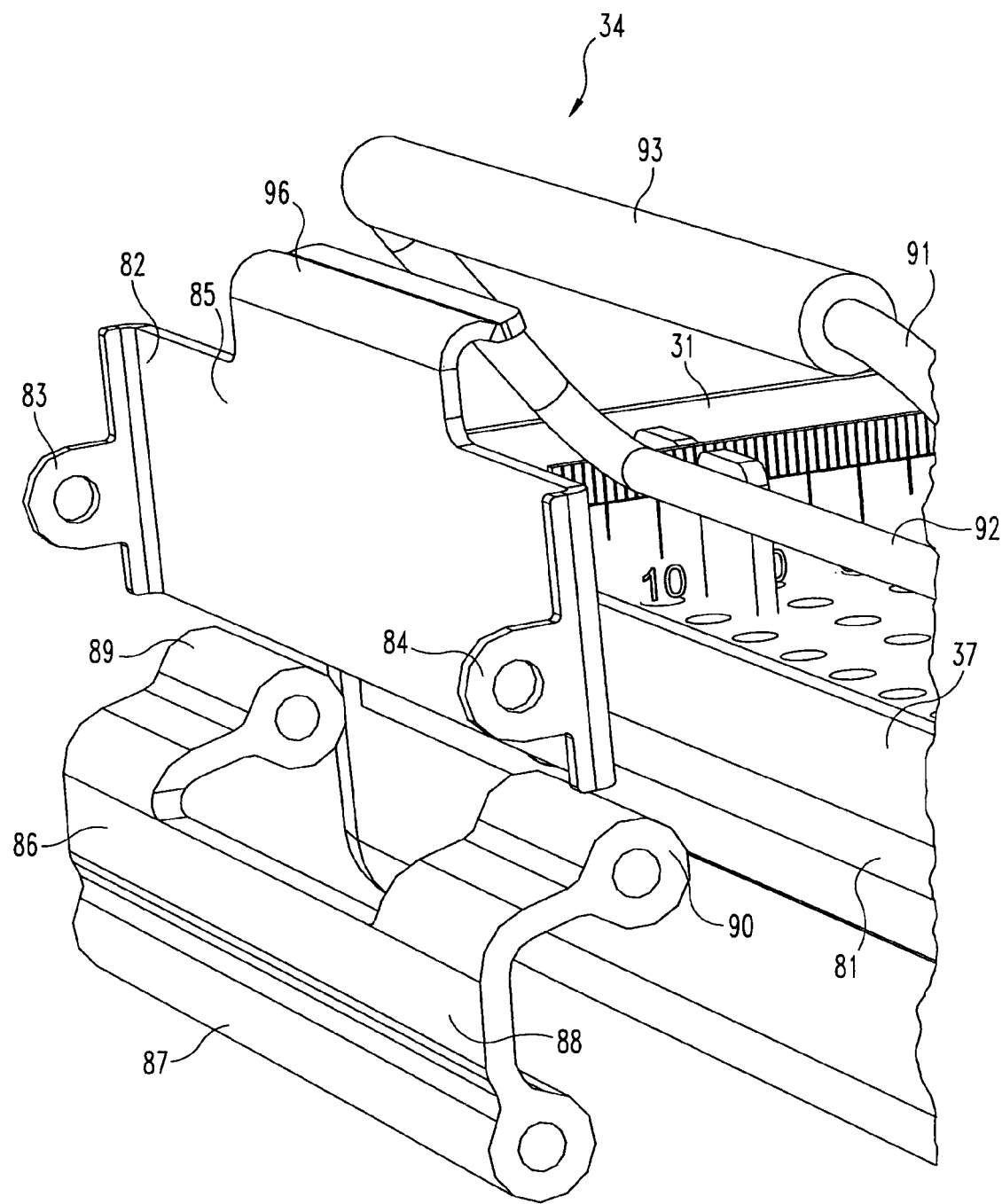
FIG. 12 is the same view as FIG. 11 only showing an exploded view of the handle with the tray assembly having the cover removed therefrom.

Assembly 34 will now be described it being understood that an identical description applies to assembly 33. Assembly 34 includes a folded sheet metal bracket 82 (FIG. 12) with a pair of ears 83 and 84 extending through rectangular opening 81 (FIG. 10) provided in wall 37. The main body 85 (FIG. 12) of bracket 82 is positioned immediately adjacent and inside wall 37. Bracket 82 has a hook shaped top end 96 that protrudes above the top of tray 31 and through the cover 32 when mounted to the tray. An elastomeric member 86, having a cross section identical to the flexible bracket 56, is mounted to bracket 82 by means of a cylindrical pin 97 (FIG. 11) that extends through ears 83 and 84 and the hollow cylindrical bottom end 87 of member 86. Member 86 has a central web 88 integral with end 87. Retaining clips similar to those used to affix the internal components to the tray floor also serve to retain pin 97 to ears 83 and 84. The clips reside in grooves on pin 97 located between the elastomeric member 86 and ears 83 and 84. It is understood that flexible bracket 56 and elastomeric member 86 are the same raw material.

A wire bail forms a handle 91 with the lower wire portion 92 of the wire bail 91 extending through the hollow centers of top ends 89 and 90 of elastomeric member 86. A tubular grip 93 receives the top opposite spaced apart ends of handle 91 and acts to cushion the gripping area of the handle assembly.

When assembly 34 is in a non-latch position, ends 89 and 90 are located vertically above web 88 and bottom end 87. Web 88 assumes the bent configuration depicted in FIGS. 11 and 12 when assembly 34 is pulled inwardly so that the bottom wire portion 92 of the handle 91 that extends through ends 89 and 90 may be retained securely beneath the hook shaped top end 96 of bracket 82. By pulling the wire bail inwardly, the elastomeric member 86 is stretched so that the wire bail bottom portion 92 may be retained securely beneath the hook shaped top end 96. Thus, the weight of the system is not carried by the elastomeric member 86 but by the bracket 82 and thus by the tray. Accidental disengagement of the wire bail handle from the hook will not result in dropping of the system and its contents. Cylindrical bottom end 87 is positioned adjacent and outwardly of wall 37. Web 88 attaches cylindrical bottom end 87 to the pair of cylindrical hollow top ends 89 and 90 that are positioned over tray 31. Ends 89 and 90 are spaced apart with hook shaped end 96 of bracket 82 positioned therebetween.

Figure 13:
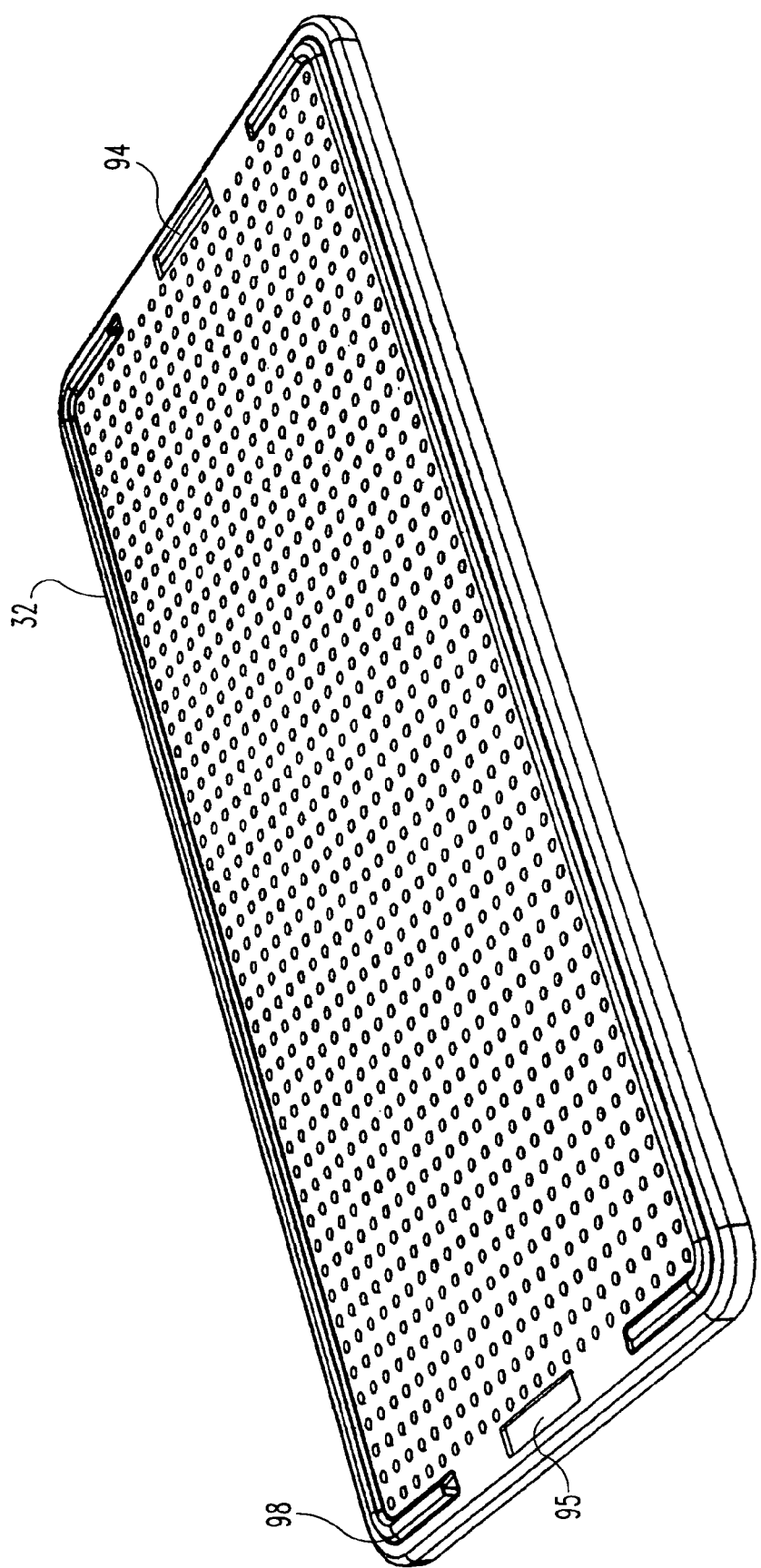
FIG. 13 is a perspective view of the cover.
Figure 14:
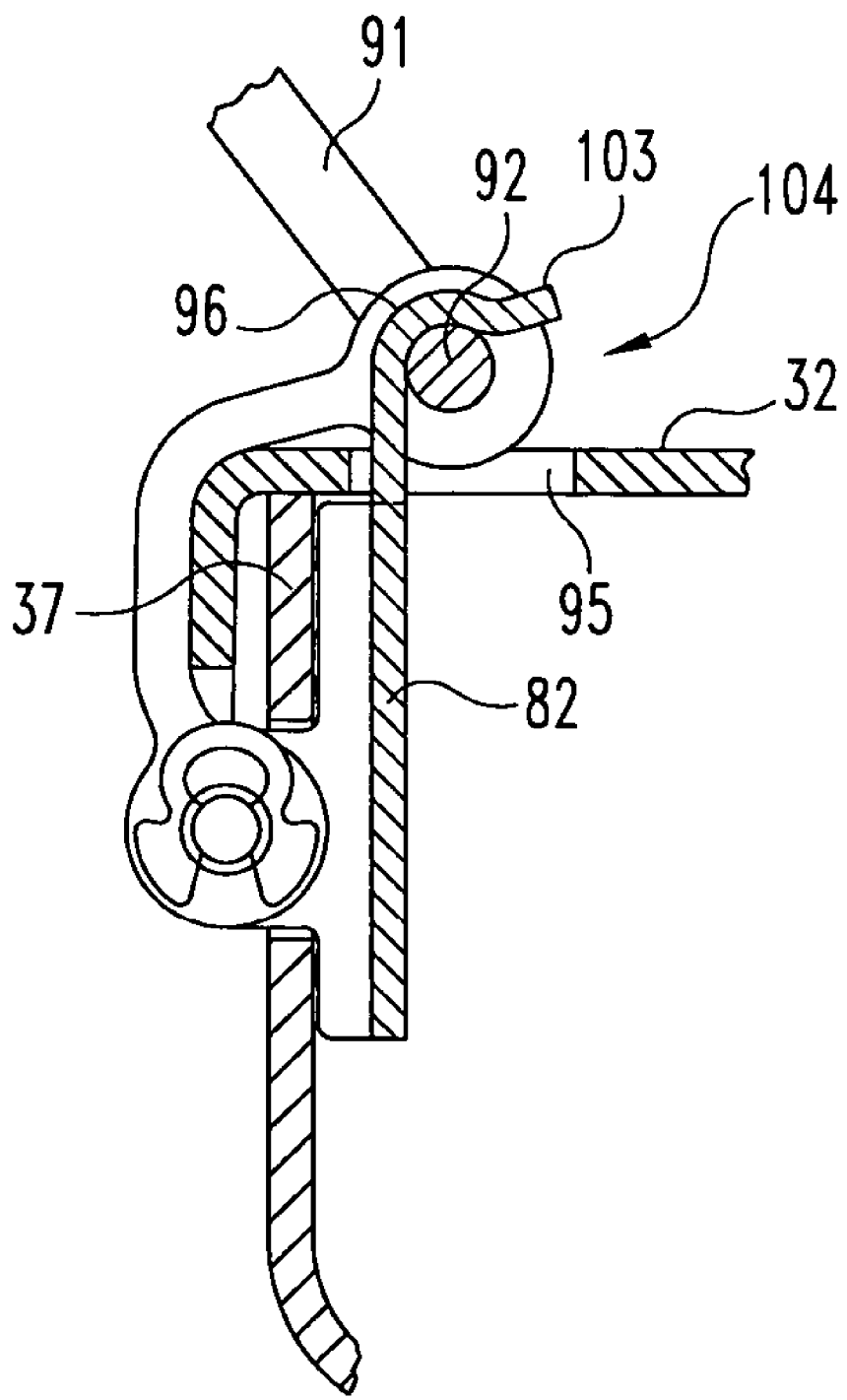
FIG. 14 is a fragmentary cross-sectional view illustrating the cover mounted to the tray with a hook-shaped end protruding through the cover and the handle positioned between the hook-shaped end and the cover.

Cover 32 may be constructed from any sterilizable, suitably rigid material. For example, the cover may be a drawn aluminum pan, fabricated from folded sheet metal or from polymer resin being molded, vacuum formed etc. The quantity and locations of perforations present in the cover must, at a minimum, match exactly those present for the fastening of internal components to the floor of a single layer system or the floor of the top insert tray in a multiple layer system. Cover 32 (FIG. 13) includes a pair of rectangular openings 94 and 95 at the opposite end portions to allow for the passage of hook shaped ends 96 of assemblies 33 and 34.

The cover is mounted to the tray when using sterile wrap in lieu of rigid container systems, as the cover is necessary to prevent the contents of the container from escaping their retaining brackets when the system is tumbled during the wrapping process.

When installing the cover to the tray, ends 111 of the posts 108 are extended into or through the cover. Hook shaped ends 96 are extended from beneath the cover through openings 94 and 95 (FIG. 13) with the hook shaped ends then protruding over and above the cover. The holes extending through the cover and floor allow fluid sterilant flow facilitating the sterilization of the items held within the tray.

Tubular grips 93 of assemblies 33 and 34 are then grasped and pulled upwardly and then over the cover positioning bottom wire portion 92 of each handle around the edge 103 of hook shaped end 96 in the direction of arrow 104 and into and beneath the hook shaped end so that portion 92 is positioned between the hook shaped end 96 and the top of the cover. In the event the cover is not utilized, then wire portion 92 is still positioned beneath the hook shaped end 96.

With the cover mounted to the tray, the handles may rotate approximately 210 degrees from a position lying inward and flush atop the cover to a binding position extending outward of the perimeter of the cover. This binding position, achievable by carrying the system by the handles while inverted, increases the security that the handle assemblies will remain engaged in the retained cover position. The method of carrying the system with or without the cover present and securing the cover when present is equally applicable to any container system of suitably rigid material having a close or flush fitting cover and appropriate openings at each end of the floor and cover. Additional characteristics include: (1) a latched or unlatched state is visually apparent, (2) one-hundred percent field repairable without the use of special tools, and (3) the system does not require precision manufacturing tolerances for optimum function.

By removing the cover from the tray, the system is properly configured when used inside present rigid container systems in lieu of sterile wrap systems. With the perforated cover mounted to the tray, the system is configured when using sterile wrap as the cover is necessary to prevent the contents of the container from escaping their retaining brackets when the system is tumbled during the wrapping process.

Cover 32 (FIG. 13) may be provided with circumferentially extending ridges 98 or other projections to promote the secure stacking of the systems by providing nesting locations for the external feet 80 when the systems are placed atop one another.

Many variations of the described structure are contemplated and included in the present invention. For example, the flexible and rigid brackets may take many shapes and configurations depending on the items to be secured. As an example, flexible bracket 130 (FIG. 5) includes a bowed web 131 integral with the opposite tubular shaped ends forming a pouch to receive the end of an instrument 132 (FIG. 7). Further as an example, spaced apart posts 133 and 134 (FIG. 7) include an outer silicone casing extending around posts 108 to receive the ring shaped ends 135 and 136 (FIG. 7) of an instrument.

When mounting the various surgical instruments, implants and devices in the tray, it is helpful for the user to know where the particular device is to be mounted within the tray. Thus, we have provided labels associated with the flexible and rigid brackets. The labels may consist of a flat plate 140 (FIG. 20) made from a metal, plastic or paper material and having the indicia 141 provided on the upwardly facing surface of the label identifying the particular device to be mounted to the bracket. The indicia may consist of a bar code, letters or numbers or any type of identifying marks. The indicia may be placed on the plate by printing, etching or any conventional technique. The thickness of the plate is such that the ends of the plate fit between the floor 35 of the tray and the head of button fastener 53 and between the floor 35 of the tray and shoulder 117 (FIG. 17) of bracket mounting post 108. The thickness of plate 140 may be equal to the length of reduced portion 116 of post 108. Thus, the labels may be utilized with the rigid brackets and/or flexible brackets previously described.

Figure 21:
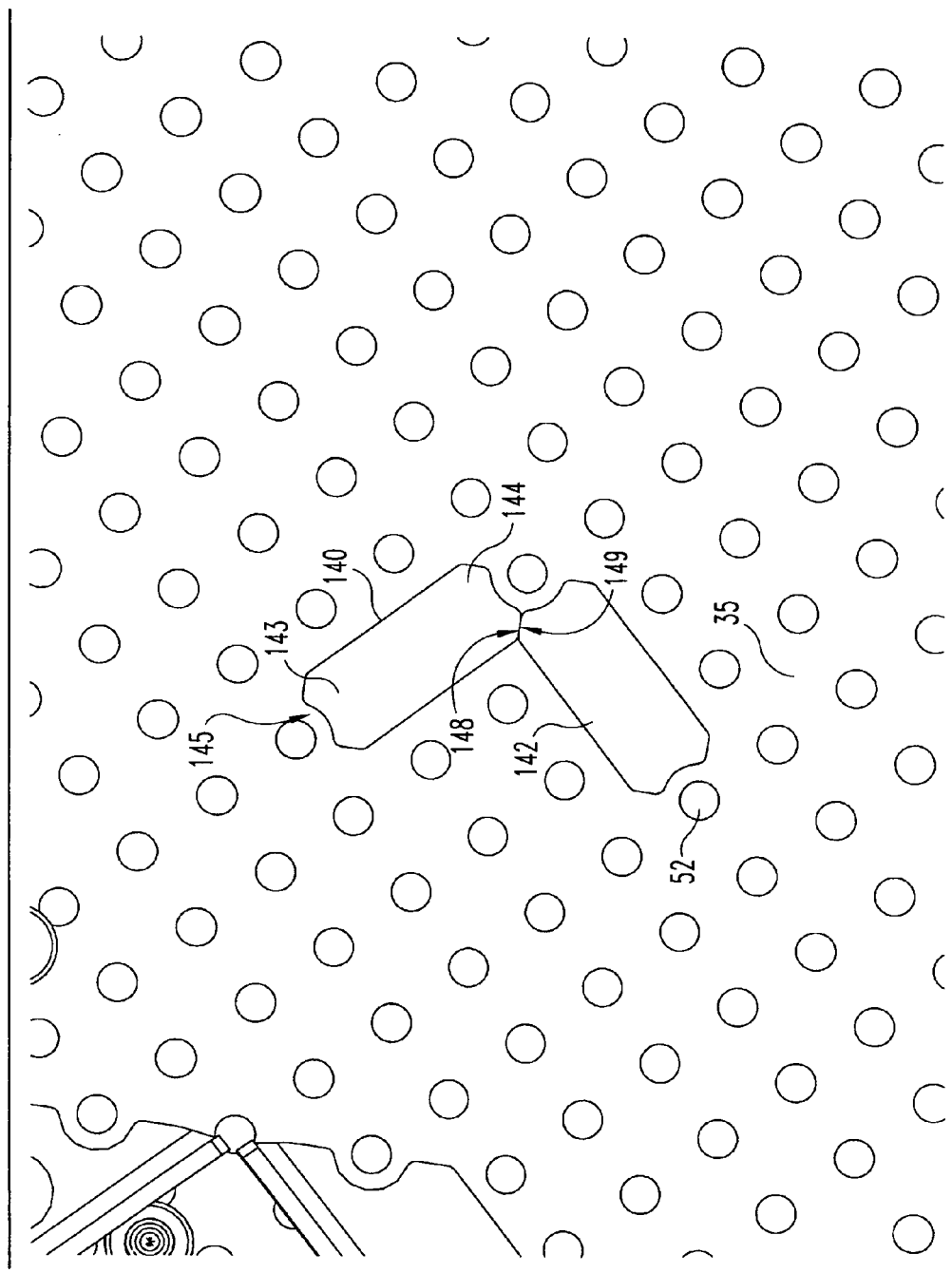
FIG. 21 is a top view of two of the labels illustrated in FIG. 20 with the bracket and, mounting posts and button fastener removed.
Figure 22:
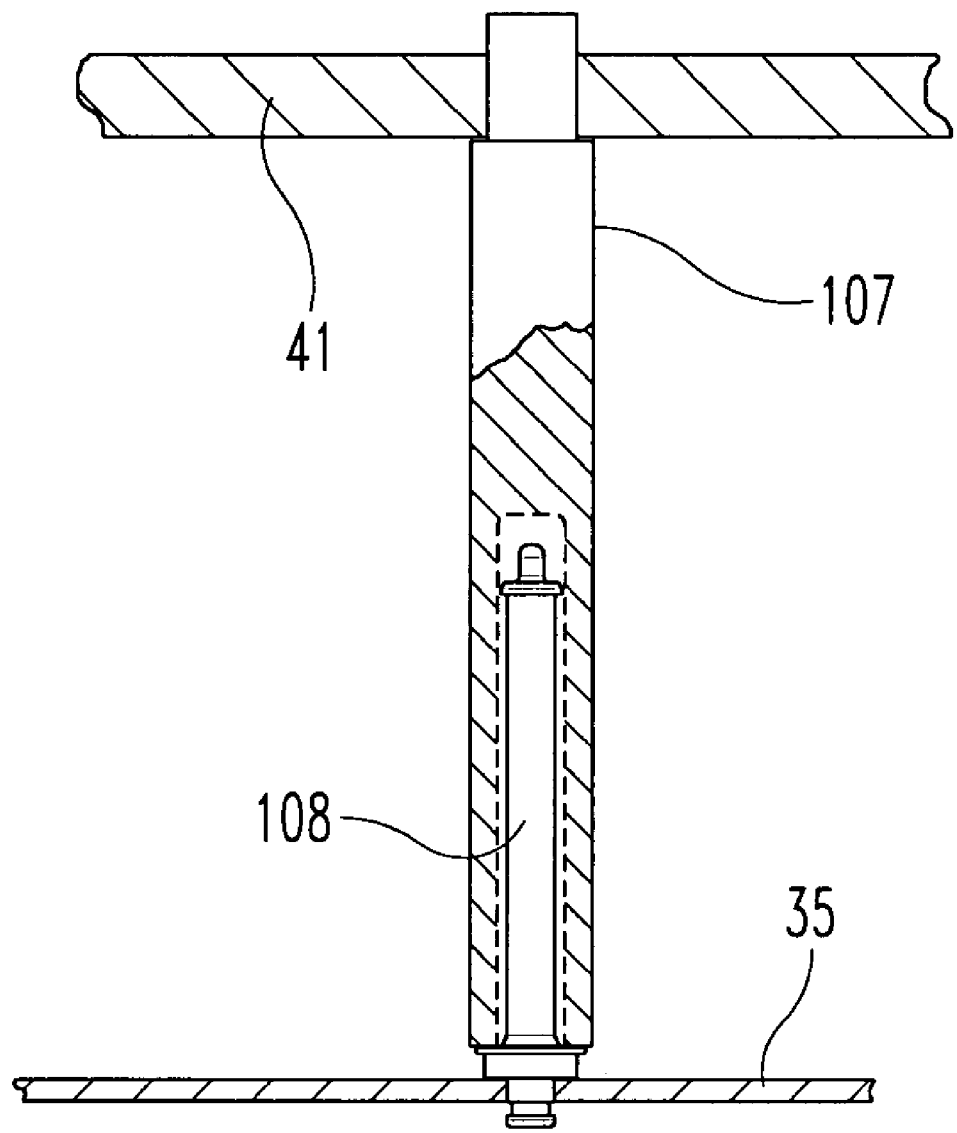
FIG. 22 is an enlarged cross sectional view of the fixture post mounted to the fixture receiving the bracket post mountable to the tray floor.

Label plate 140 has a pair of opposite beveled ends 143 and 144 (FIG. 21) with a curved recess 145 to partially receive the shank of button fastener 53 and post 108. The width 146 of plate 140 equals the distance 147 between the centers of adjacent holes 52 of floor 35 to allow positioning of adjacent plates extending between rows of adjacent holes 52. Plate 142 is shown positioned beneath a flexible bracket 56 and extending out from either side of the flexible web of the bracket to allow label indicia to be provided on the label to show on the opposite sides of the flexible web. The beveled edges 148 and 149 of labels 140 and 142 allow locating the labels and brackets at right angles relative to each other thereby allowing for a wide variety of positioning of the brackets atop the floor.

Figure 20:
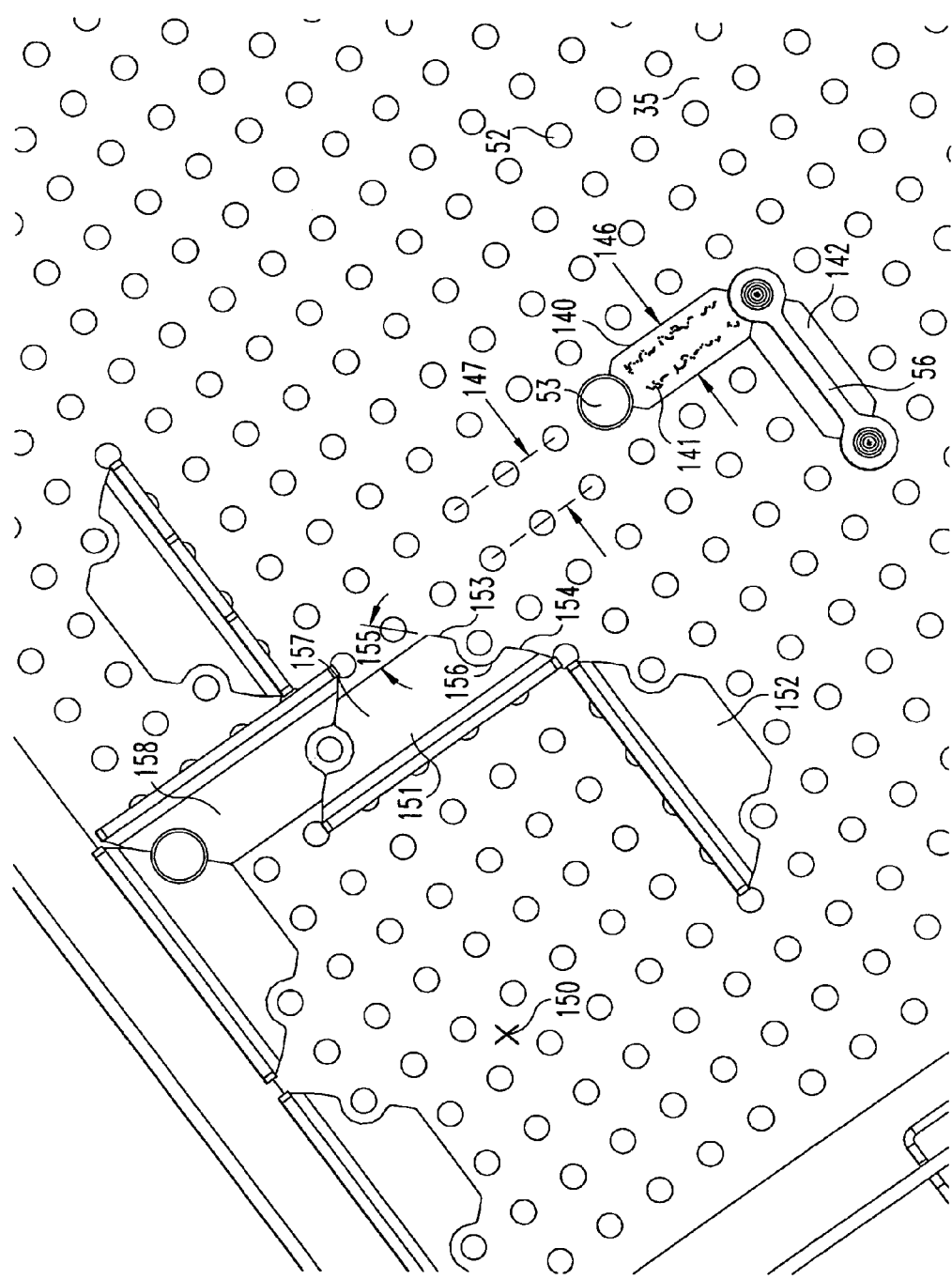
FIG. 20 is an enlarged fragmentary top view of the tray illustrating labels positioned beneath rigid and flexible brackets as well as an alternate embodiment of the rigid bracket.

A variation of the rigid bracket is shown in FIG. 20. Brackets 151 and 152 are identical to brackets 55 and 70 previously described except that the opposite end edges of the wall 157 resting atop floor 35 are formed at forty-five degree angles 155 relative to the bracket longitudinal axis extending the length of the bracket creating at the opposite ends of each bracket a pair of edges 154 and 153 between which is formed curved recess 156 to receive the shank of the button fastener 53. Edges 154 and 153 may also be in contact with the beveled end edges of the labels. For example, a label 140 having edge 149 may be positioned so edge 149 contacts edge 153 of bracket 151 with a fastener 53 then securing label 140 to the tray floor. Thus, the labels may be utilized with both rigid brackets and flexible brackets. Some of the button fasteners are removed in FIG. 20 from the brackets to illustrate the bracket edges. A pair of brackets 151 and 158 may be aligned in a row with their end edges in contact with each minimizing the space occupied by adjacent brackets. The brackets may be arranged to form areas or compartments, for example area 150, in which are located specific types of items to be held by the brackets.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A container for use in holding, sterilizing and delivering medical devices and implants comprising:
    a perforated floor having a plurality of floor holes, said floor forming a cavity to receive medical devices and implants;
    a perforated cover having a plurality of apertures being removably mounted to said floor;
    a plurality of mounts with proximal ends movably mounted to said floor within said cavity at said holes;

a plurality of brackets mounted to said mounts to removably hold medical devices and implants to said floor within said cavity; and, handle assemblies mounted to said floor and having fixed portions extending over said floor and further having movable portions movable from a first position apart from said fixed portions to a second position beneath and adjacent to said fixed portions, said movable portions in said second position between said cover and said fixed portions when said cover is mounted to said floor to releasably hold said cover to said floor; and wherein:

said cover includes a pair of handle openings; and, said assemblies include hook shaped top ends fixedly mounted to said floor that extend from beneath said cover and through said handle openings, said movable portions include wire bails pivotally mounted to said floor and positionable between said hook shaped top ends and said cover to releasably hold said cover on said floor.

2. The container of claim 1 wherein:
said assemblies include flexible portions having bottom ends mounted to said floor and top ends with said wire bails mounted thereto isolating said cover from any lifting force applied to said wire bails, said flexible portions bendable as said wire bails move from said first position to said second position.

3. The container of claim 2 wherein said floor includes:
feet extending beneath said floor.

4. The container of claim 3 wherein:
said cover includes an outwardly facing surface with nesting portions formed thereon to removably receive said feet allowing stacking of containers.

5. A container for use in holding, sterilizing and delivering medical devices and implants comprising:
a perforated floor having a plurality of floor holes, said floor forming a cavity to receive medical devices and implants;
a perforated cover having a plurality of apertures being removably mounted to said floor;
a plurality of mounts with proximal ends movably mounted to said floor within said cavity at said holes;
a plurality of brackets mounted to said mounts to removably hold medical devices and implants to said floor within said cavity; and,
handle assemblies mounted to said floor and having fixed portions extending over said floor and further having movable portions movable from a first position apart from said fixed portions to a second position beneath and adjacent to said fixed portions, said movable portions in said second position between said cover and said fixed portions when said cover is mounted to said floor to releasably hold said cover to said floor; and wherein:
said mounts are bracket posts with distal ends and further comprising a fixture with a plurality of fixture holes alignable with said floor holes, and further comprising a plurality of hollow fixture posts mounted to said fixture at said fixture holes, said fixture posts sized to receive said bracket posts for mounting said bracket posts to said floor.

6. The container of claim 5 wherein:
said distal ends of said bracket posts are alignable with said apertures of said cover to allow support of said bracket posts by said cover.

7. The container of claim 6 wherein:
said proximal ends extend through and project outwardly of said floor; and, further comprising,
mounting devices including external clips positionable adjacent and outwardly of said floor removably holding said bracket posts to said floor.

8. The container of claim 7 wherein:
said brackets include passages in which said bracket posts extend mounting said brackets thereto atop said floor.

9. The container of claim 8 wherein said apertures are aligned with said floor holes.

10. The container of claim 9 wherein:
some of said floor holes and apertures are open to allow fluid flow there through.

11. A container for use in holding medical devices comprising:
a tray with a bottom wall and upwardly extending side walls forming a cavity to receive medical devices, said bottom wall including a plurality of bottom wall holes extending there through to allow fluid flow;
a cover removably mountable to said tray with cover holes to allow fluid flow;
a plurality of brackets removably mounted to said bottom wall;
a pair of handle assemblies mounted to said tray with at least one of said assemblies including:
a rigid hook shaped member mounted to said tray and extending above said cavity;
a stretchable member mounted to said tray;
a handle mounted to said stretchable member and movable by stretching said stretchable member to position said handle immediately beneath and adjacent said rigid hook shaped member to allow lifting forces applied to said handle to be applied to said hook shaped member, said cover when mounted to said tray having a slot through which said hook shaped member projects upwardly there through forming a recess between said hook shaped member and said cover in which said handle is positionable holding said cover to said tray.

12. A container for holding medical items comprising:
a tray with a perforated bottom wall and upwardly extending side walls forming a cavity to receive medical items, said tray having a hook extending above said cavity, said hook forming a recess;
a perforated cover removably mountable to said side walls and having a slot through which said hook is extendable forming a recess between said lid and hook;
brackets removably mounted to said bottom wall within said cavity to hold medical items; and,
a handle movably mounted to said tray and having a portion positioned beneath and against said hook to transfer handle lifting force to said hook and tray, said portion positioned between said hook and said cover when said cover is mounted to said tray to hold said cover to said tray while isolating said cover from handle lifting force.

13. The container of claim 12 and further comprising:
a stretchable member mounted to and between said tray and said handle, said stretchable member has a stretched position when said portion of said handle is located beneath and against said hook biasing with said hook said portion of said handle within said recess.

14. The container of claim 12 and further comprising:
a plurality of posts with distal ends and proximal ends with said proximal ends removably mounted to said bottom wall, said posts extending through said brackets holding said brackets within said tray; and, fasteners mounted to said distal ends of said posts holding said brackets to said posts and extendable into said cover.

15. The container of claim 12 wherein:

said brackets are produced from silicone and are supported along their height from said bottom wall of said tray to said cover, said brackets including openings to loosely receive and hold medical items.

16. A container for holding medical items comprising:

a tray with a perforated floor and upwardly extending side walls forming a cavity to receive medical items, said tray having a hook extending above said cavity, said hook forming a recess;

brackets removably mounted to said floor within said cavity to hold medical items;

a handle movably mounted to said tray and having a portion positioned beneath and against said hook to transfer handle lifting force to said hook and tray;

a plurality of posts with distal ends and proximal ends with said proximal ends removably mounted to said floor, said posts extending through said brackets holding said brackets within said tray;

fasteners mounted to said distal ends of said posts holding said brackets to said floor;

a stretchable member mounted to and between said tray and said handle, said stretchable member has a stretched position when said portion of said handle is located beneath and against said hook biasing with said hook said portion of said handle within said recess.

17. A container for holding medical items composing:

a tray with a perforated floor and upwardly extending side walls forming a cavity to receive medical items, said tray having a hook extending above said cavity, said hook forming a recess;

a handle movably mounted to said tray and having a portion positioned beneath and against said hook to transfer handle lifting force to said hook and tray; and, a stretchable member mounted to and between said tray and said handle, said stretchable member has a stretched position when said portion of said handle is located beneath and against said hook biasing with said hook said portion of said handle within said recess.

* * * * *